US009400161B2

(12) United States Patent
Cha et al.

(10) Patent No.: US 9,400,161 B2
(45) Date of Patent: Jul. 26, 2016

(54) OCT PROBE USING PZT

(75) Inventors: Hyun Rok Cha, Gwangju (KR); Dae Yeong Im, Jeollanam-do (KR); Jae Young Ahn, Gwangju (KR); Hyoung Uk Nam, Gwangju (KR); Tae Won Jeong, Gwangju (KR)

(73) Assignee: Korea Institute of Industrial Technology, Cheonan-si, Chungcheongnam-do (KR)

( * ) Notice: Subject to any disclaimer, the term of this patent is extended or adjusted under 35 U.S.C. 154(b) by 175 days.

(21) Appl. No.: 13/997,912

(22) PCT Filed: Aug. 8, 2012

(86) PCT No.: PCT/KR2012/006295

§ 371 (c)(1), (2), (4) Date: May 30, 2014

(87) PCT Pub. No.: WO2013/172509

PCT Pub. Date: Nov. 21, 2013

(65) Prior Publication Data

US 2014/0300901 A1 Oct. 9, 2014

(30) Foreign Application Priority Data

May 17, 2012 (KR) ........................ 10-2012-0052617

(51) Int. Cl.

| | |
|---|---|
| ***G01B 9/02*** | (2006.01) |
| ***G01B 1/00*** | (2006.01) |
| ***A61B 5/00*** | (2006.01) |
| ***G01N 21/47*** | (2006.01) |
| ***A61B 1/00*** | (2006.01) |

(52) U.S. Cl.

CPC .............. *G01B 1/00* (2013.01); *A61B 1/00096* (2013.01); *A61B 1/00112* (2013.01); *A61B 1/00165* (2013.01); *A61B 1/00172* (2013.01); *A61B 5/0066* (2013.01); *G01B 9/0205* (2013.01); *G01B 9/02091* (2013.01); *G01N 21/4795* (2013.01); *A61B 2562/0233* (2013.01); *G01B 2290/65* (2013.01)

(58) Field of Classification Search

CPC .... G01B 2290/65; G01B 1/00; G01B 9/0205; G01B 9/02091; A61B 1/00172; A61B 1/00096; A61B 1/00165; A61B 1/00112; A61B 5/0066; A61B 2562/0233; G01N 21/4795

See application file for complete search history.

(56) References Cited

U.S. PATENT DOCUMENTS

| | | | | |
|---|---|---|---|---|
| 7,496,259 | B2 * | 2/2009 | Karasawa .......... | A61B 1/00096 385/118 |
| 2011/0257486 | A1 | 10/2011 | Chang et al. | |

FOREIGN PATENT DOCUMENTS

| | | |
|---|---|---|
| JP | 2002272674 A | 9/2002 |
| JP | 2007171021 A | 7/2007 |
| JP | 2009172118 A | 8/2009 |

* cited by examiner

*Primary Examiner* — Hwa Lee

(74) *Attorney, Agent, or Firm* — Reinhart Boerner Van Deuren P.C.

(57) ABSTRACT

An optical coherence tomography (OCT) probe using lead zirconate titanate (PZT). In the OCT probe using PZT, a sine wave is induced from a vibrator made of a piezoelectric element, so that an image in which the scanning range is increased can be captured due to the vibration of the vibrator. A decrease in the vibration of the vibrator can be minimized by optimizing the position where the base fixes the vibrator.

4 Claims, 4 Drawing Sheets

100 126 124 122 140a 160 130 132 140b 150 110

OCT PROBE USING PZT

TECHNICAL FIELD

The present invention relates to an optical coherence tomography (OCT) probe using lead zirconate titanate (PZT), and more particularly, to an OCT probe using PZT, in which a sine wave is induced from a vibrator made of a piezoelectric element, so that an image in which the scanning range is increased can be captured due to the vibration of the vibrator, and a decrease in the vibration of the vibrator can be minimized by optimizing the position where the base fixes the vibrator.

BACKGROUND ART

Recently, the development of an optical coherence tomography (OCT), which can provide higher resolution than an ultrasonic imaging system while having a simpler structure than computed tomography (CT) or magnetic resonance imaging (MRI), is underway.

An OCT system is a system that captures a tomographic image of a multiple scattering object, such as a living body, by emitting low-coherence light similar to natural light the object to and detecting the light reflected from the object.

The OCT system captures an image of a subject by emitting light to a multiple scattering object, such as a living body, using a probe. For the probe, a variety of methods are being attempted, based on various structures, including a polygon mirror, a Galvanometer mirror and a micro-electro-mechanical system (MEMS) mirror. In particular, active studies on methods of applying an optical fiber to the probe in order to capture a topographic image of a subject are underway.

However, the probe employing the optical fiber of the related art scans part of an area to be scanned instead of scanning the entire area.

Therefore, there are problems in that more correct information about the area to be scanned cannot be acquired, and that more scanning time is required when attempting to scan the entire area.

DISCLOSURE

Technical Problem

The present invention has been made to solve the foregoing problems with the prior art, and therefore an object of the present invention is to provide an optical coherence tomography (OCT) probe using lead zirconate titanate (PZT), which can increase the scanning range of light that is emitted to a subject using a piezoelectric vibrator which vibrates up and down and to the left and to the right when a sine wave is induced thereto.

In addition, the invention is intended to provide an OCT probe using PZT, which can acquire a wider scanning range by optimizing the position where a base fixes the vibrator such that the vibrator can vibrate.

Technical Solution

In order to realize the foregoing object, the invention provides an OCT probe using PZT, which includes: an outer case having defined an inner space therein and extending a predetermined length; a vibrator having a hollow body made of a piezoelectric element, the body extending a predetermined length, and a plurality of electrodes arranged on an outer circumference of the body in a circumferential direction such that the hollow body can be vibrated in response to the voltage of a sine wave induced thereto, the electrodes being connected with cables; a base arranged at a predetermined distance outside the body via a support member having a predetermined height such that the base surrounds a part of the body, the base being fixedly disposed inside the case to fix a part of the vibrator; and an optical fiber arranged to extend through an inside of the body such that the optical fiber emits light to a subject and receives the light reflected or scattered from the subject, an intermediate portion of the optical fiber being fixed by a ferrule inserted a predetermined depth into one end of the body.

It is preferred that one end of the support member support the base at a point where the amplitude of the sine wave is 0.

It is preferred that the support member supports a point that is 3/20 of a total length of the body.

It is preferred that a lens be additionally provided in the inner space, the lens being positioned in front of one end of the optical fiber so as to collect the light emitted from the optical fiber.

It is preferred that the base have cable slits in an outer surface thereof, the cable slits being cut open a predetermined depth in a longitudinal direction such that the cables connected to the electrodes are inserted into and seated in the cable slits.

Advantageous Effects

According to the invention, the probe can capture not only two-dimensional (2D) images but also three-dimensional (3D) images since it uses the piezoelectric vibrator which vibrates up and down and to the left and to the right when a sine wave is induced thereto.

In addition, according to the invention, a wider scanning range can be acquired by optimizing the position where a base fixes the vibrator such that the vibrator can vibrate.

DESCRIPTION OF DRAWINGS

FIG. 3A to FIG. 3C are graphs showing variations in amplitude depending on the position where a base fixes a vibrator in an OCT probe using PZT according to the invention, in which FIG. 3A shows the case where the vibrator is fixed before a point where the amplitude of a sine wave is 0, FIG. 3B shows the case where the vibrator is fixed at the point where the amplitude of the sine wave is 0, and FIG. 3C shows the case where the vibrator is fixed after the point where the amplitude of the sine wave is 0.

MODE FOR INVENTION

Figure 1:
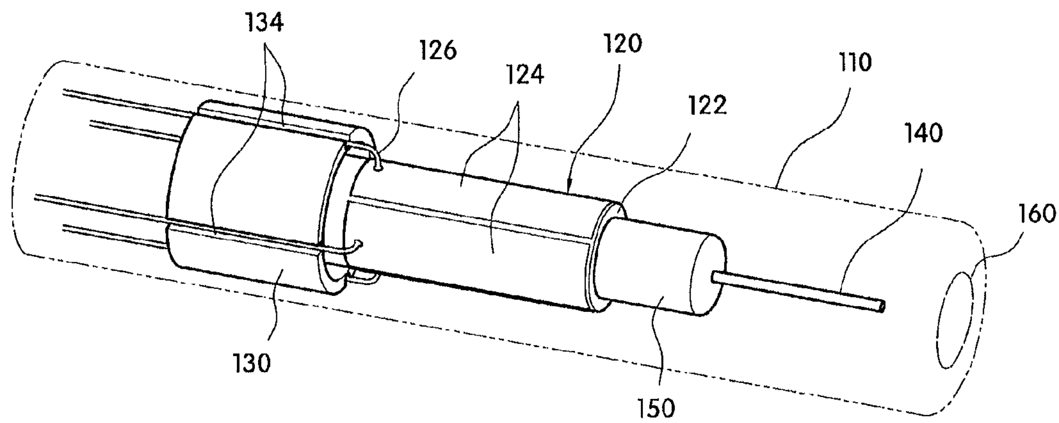
FIG. 1 is an overall perspective view showing an OCT probe using PZT according to the invention.

Hereinafter, exemplary embodiments of the invention will be described in more detail with reference to the drawings.

In the following description, when reference numerals are added for better understanding of the invention, the same reference numerals and signs are used throughout the different drawings to designate the same or similar components.

An OCT probe 100 using PZT according to an exemplary embodiment of the invention has a vibrator 120 made of a piezoelectric element (PZT), the vibrator 120 vibrating up and down and to the left and to the right when a sine wave is induced thereto. The OCT probe 100 can capture a three-dimensional (3D) image using a simple structure, based on only horizontal and vertical axis driving of the vibrator 120.

The OCT probe 100 includes an outer case 110, the vibrator 120, a base 130, a ferrule 150 and an optical fiber 140.

The vibrator 120 serves to vibrate the optical fiber 140, the intermediate portion thereof in the longitudinal direction being fixed by the ferrule 150, up and down and to the left and to the right when a voltage is induced thereto. The vibrator 120 includes a hollow body 122 having a predetermined length and a plurality of electrodes 124 to which cables 126 are connected such that the electrodes 124 can be supplied with a voltage from the outside. The body 122 is made of a piezoelectric element, such as $PbZrO_4$, and has a hollow shape such that the optical fiber 140 can be disposed inside and pass through the body 122. One end of the body 122 is fixed by the base 130, such that the other end of the body 122 to which the ferrule 150 is coupled can vibrate at predetermined amplitude when the voltage is induced thereto. In addition, the plurality of electrodes 124, which are connected with the cables 126 such that they can be supplied with the voltage from the outside, are provided in the circumferential direction on the outer circumference of the body 122.

The plurality of electrodes 124 are spaced apart from each other at predetermined distances in the circumferential direction of the body 122 such that they are electrically isolated from each other. It is preferred that the electrodes 124 be configured as four poles such that the body 122 can vibrate along both the longitudinal axis and the lateral axis, thereby drawing a circular trace, when the voltage is supplied via the cables 126.

The four pole electrodes are divided into two electrode pairs, each of which includes two poles, along the X axis and the Y axis. When the direct current (DC) power of a sine wave is supplied to each axis, the vibrator 120 starts vibrating. When the vibrator 120 operates, the vibrator 120 starts vibrating at the amplitude, and the optical fiber 140 fixed by the ferrule 150 circularly operates due to the amplitude.

Here, in order for light emitted from the optical fiber 140 to form a precise perfect circle, the voltage and the current supplied to the vibrator 120 must have the same frequency. Resonance occurs when the voltage and the current supplied to the vibrator 120 have the same frequency and the phases are the same. In general, the resonance causes the amplitude to be the greatest. In addition, in order to form this perfect circle, the difference in the phase of resonance between the X axis and the Y axis must be 90°.

Figure 2:
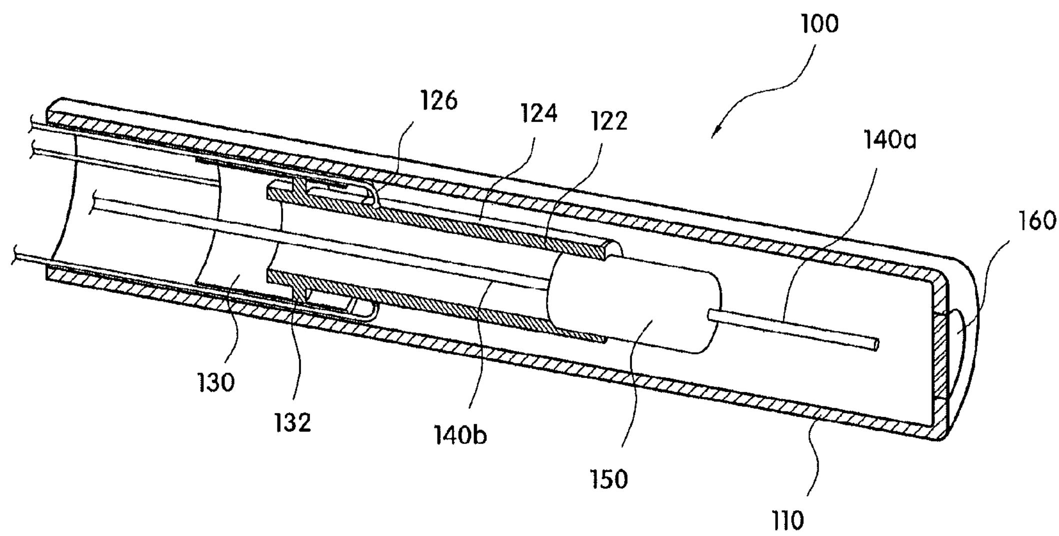
FIG. 2 is a longitudinal cross-sectional view of FIG. 1.

The base 130 serves to surround and fix a part of the vibrator 120 so that the other end of the vibrator 120 to which the ferrule 150 is coupled can freely vibrate, and provides a space that maintains a distance from the inner surface of the outer case 110 so that the other end of the vibrator 120 to which the ferrule 150 is coupled can vibrate at predetermined amplitude. That is, the base 130 is configured as a cylinder that has a predetermined length and an inner diameter greater than the outer diameter of the body 122. As shown in FIG. 2, the base 130 is connected to the body 122 via support members 132 having a predetermined height.

In the state where the base 130 is coupled by the outer case 110 as above, when a voltage is induced to the electrodes 124, the other end of the vibrator 120 coupled with the ferrule 150 can freely vibrate since one end of the body 122 is fixed by the support members 132.

In addition, the base 130 has a plurality of cable slits 134 along the circumferential direction in the outer surface thereof, the cable slits being cut open a predetermined depth in the longitudinal direction. The cable slits 134 are formed such that the cables 126, which are connected to the electrodes 124 to supply a voltage to the vibrator 120, are inserted into the cable slits 134. Due to this configuration, the cables 126 are inserted into the cable slits 134 and do not protrude therefrom, thereby preventing the cables 126 from being damaged by the surface contact between the outer circumference of the base 130 and the inner surface of the outer case 110, which occurs when the base 130 is coupled with the outer case 110. This also facilitates coupling the base 130 and the outer case 110.

Here, it is preferred that the base 130 and the support members 132 be formed integrally with the body 122. However, this configuration is not intended to be limiting. Rather, it should be understood that only the base 130 and the support members 132 can be formed integrally with each other such that one end of each of the support members 132 is fixed to the body 122 via an adhesive or the like.

The ferrule 150 is inserted a predetermined depth into the end of the body 122, and serves to hold an intermediate portion of the optical fiber 140 in the longitudinal direction, the optical fiber 140 passing through the body 122. According to the invention, the optical fiber 140 is connected to the light source, and serves to emit light to a subject and receive the light reflected or scattered from the subject. The cover of the other end of the optical fiber which is not connected to the light source is peeled off. The portion of the optical fiber which is peeled off passes through the inside of the ferrule 150, and is fixed in position by the ferrule 150, such that it can be positioned at the center of the inside of the outer case 110, thereby preventing the core portion of the optical fiber 140, the cover of which is peeled, from being damaged through contact with the inner surface of the outer case 110 when the vibrator 120 vibrates.

The outer case 110 is configured such that it has defined an inner space therein and extends a predetermined length. The assembly, which is realized by coupling the ferrule 150 through which the optical fiber 140 has passed and the base 130 to the vibrator 120, is seated in the inner space in order to protect the assembly and fix the base 130. In particular, the assembly protects the core of the optical fiber, the cover of which is peeled off, since the core of the optical fiber 140 is fragile. This configuration also allows a user to easily hold the assembly.

In addition, it is preferred that a lens 160 be provided at the side of the end of the outer case 110 such that light emitted from the optical fiber 140 can be collected. The lens 160 is positioned in front of the end of the optical fiber 140, the cover of which is peeled off.

The invention as described above has an effect in that the probe can capture not only two-dimensional (2D) images but also 3D images since it uses the piezoelectric vibrator which vibrates up and down and to the left and to the right when a sine wave is induced thereto.

In addition, in the OCT probe 100 using PZT according to the invention, it is preferred that the position of the base 130 which is coupled to the outer case 110 and fixedly supports the end side of the vibrator 120, more specifically, the end of the support members 132 connected to the body 122 be positioned at a point where the amplitude of the sine wave is 0. When the sine wave voltage is induced, the vibrator 120 circularly vibrates while vibrating up and down and to the left and to the right. The invention can minimize vibration damping by forming the structure which supports the vibrator 120 is disposed at the point where the amplitude of the sine wave is 0, thereby maximizing the vibration of the optical fiber 140 fixed to the ferrule 150. Preferably, the base 130 is configured such that the support member 132 fixes the body 122 at the point that is 3/20 of the total length of the body.

Figure 3A:
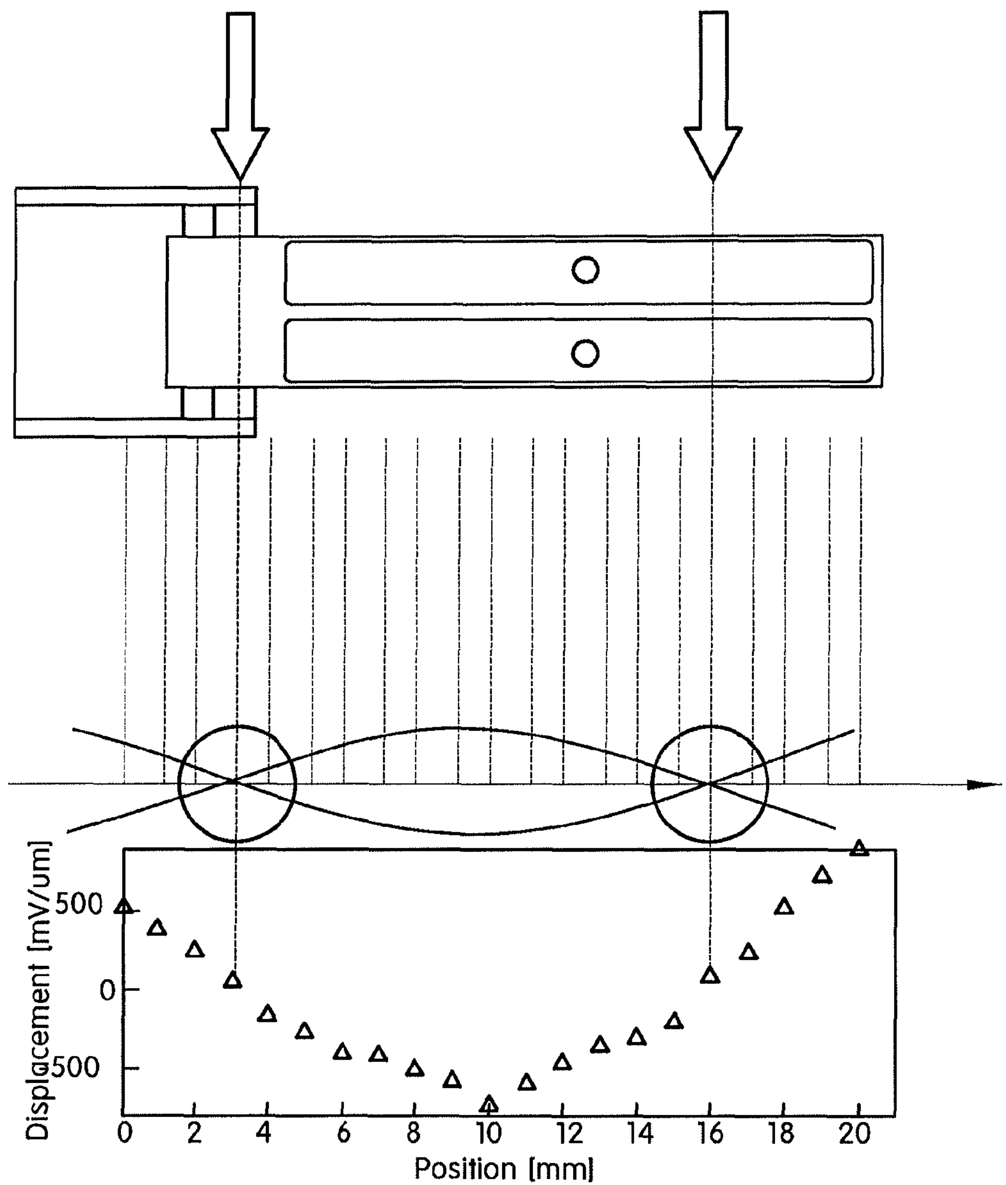
Figure 3B:
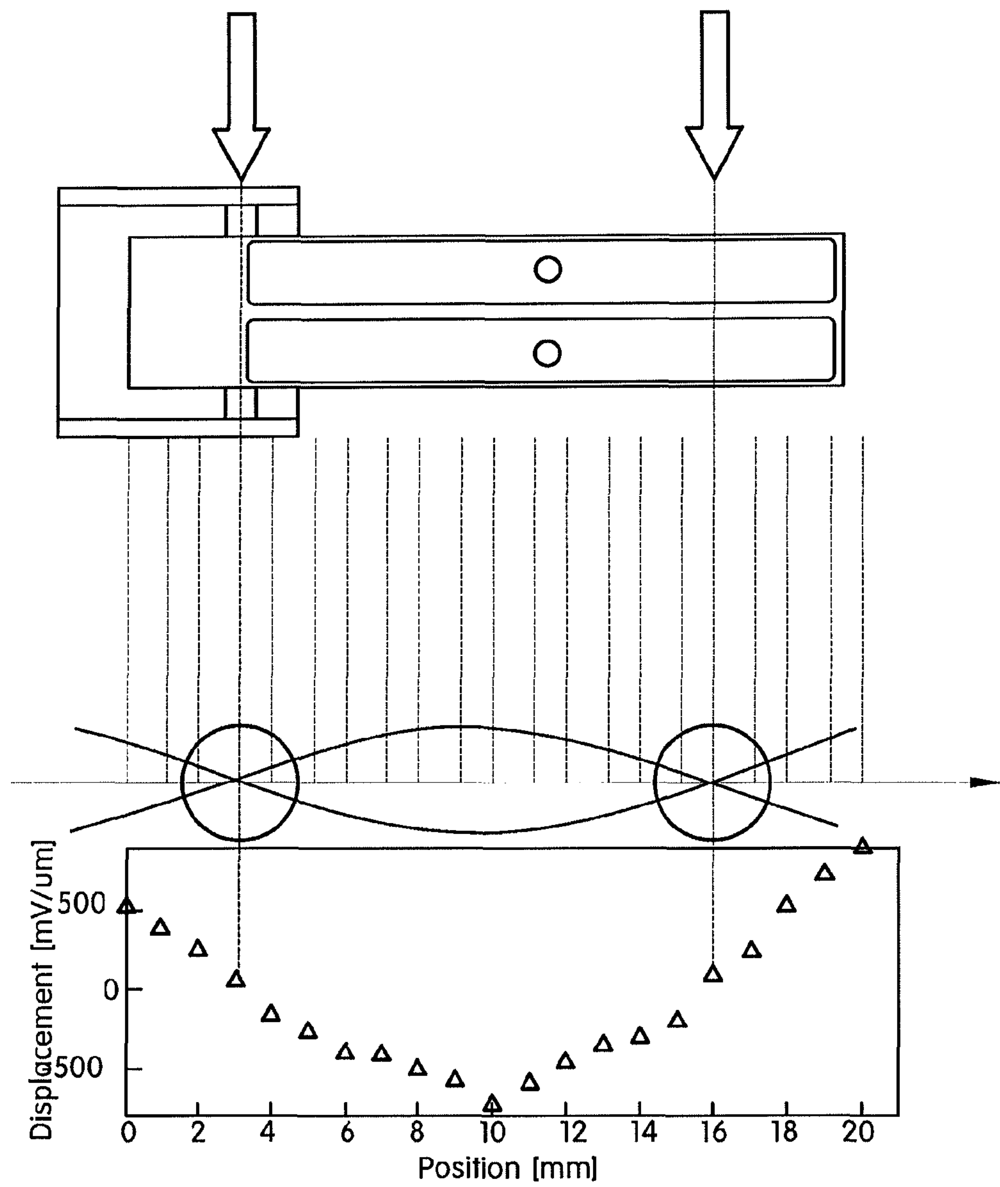
Figure 3C:
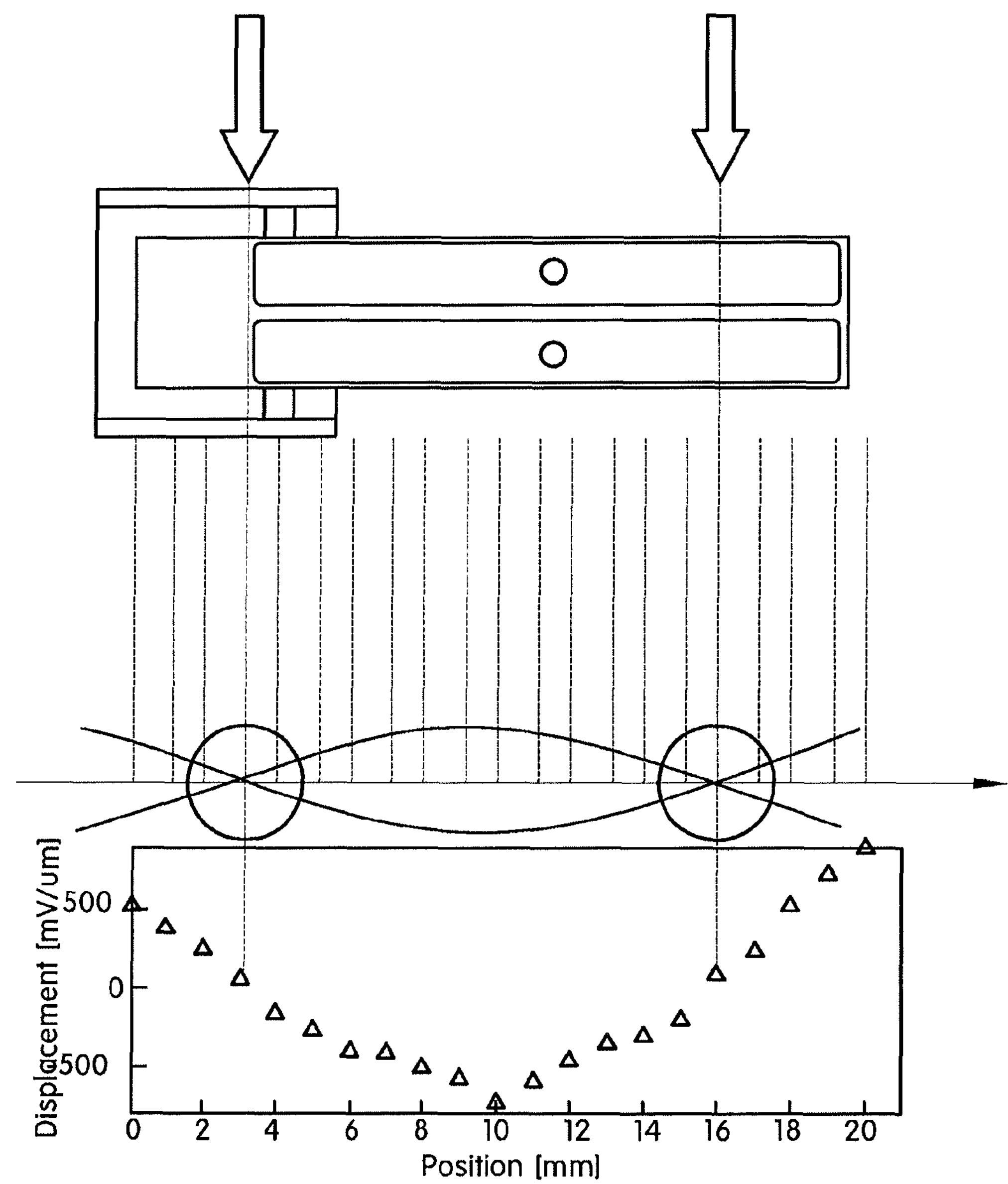

FIG. 3A to FIG. 3C are graphs showing variations in the amplitude of the optical fiber depending on the position where the support member 132 fixes the vibrator 120, in which FIG. 3A shows the case where the vibrator is fixed before a point where the amplitude of a sine wave is 0, FIG. 3B shows the case where the vibrator is fixed at the point where the amplitude of the sine wave is 0, and FIG. 3C shows the case where the vibrator is fixed after the point where the amplitude of the sine wave is 0.

Here, the total length of the body 122 is 20 mm, and when the sine wave voltage was supplied, the amplitude of the sine wave was 0 at the point that is 3 mm from the end of the body 122.

Referring to this, it can be appreciated that, when the sine wave voltage is supplied to the vibrator 120, the other end of the vibrator 120 vibrates at the greater amplitude when the vibrator is fixedly supported at the point where the amplitude of the sine wave is 0 (i.e. the point that is 3 mm from the end of the body) using the support member 132 and the base 130 than when the vibrator is supported at the point before the amplitude of the sine wave is 0 (the point that is 2 mm from the end of the body) or at the point after the amplitude of the sine wave is 0 (the point that is 2 mm from the end of the body).

As set forth above, the invention has the effect of optimizing the position where the base fixes the vibrator such that the vibrator can vibrate. This can consequently increase the radius at which the optical fiber vibrates, thereby acquiring a wider scanning range.

It is to be understood that while the present invention has been described in detail in relation to the certain embodiment, the invention is not limited to this specific structure. Rather, modifications and changes will be apparent to a person having ordinary skill in the art without departing from the principle of the invention defined in the following Claims. It is intended that all equivalents, alterations and substitutions obtained by simple design changes or modifications clearly fall within the scope of the invention.

The invention claimed is:

1. An OCT probe using PZT, comprising:

an outer case having defined an inner space therein and extending a predetermined length;

a vibrator having a hollow body made of a piezoelectric element, the body extending a predetermined length, and a plurality of electrodes arranged on an outer circumference of the body in a circumferential direction such that the hollow body can be vibrated in response to a voltage of a sine wave induced thereto, the electrodes being connected with cables;

a base arranged at a predetermined distance outside the body via a support member having a predetermined height such that the base surrounds a part of the body, the base being fixedly disposed inside the case to fix a part of the vibrator; and an optical fiber arranged to extend through an inside of the body such that the optical fiber emits light to a subject and receives the light reflected or scattered from the subject, an intermediate portion of the optical fiber being fixed by a ferrule inserted a predetermined depth into one end of the body;

wherein one end of the support member supports the base at a point where an amplitude of vibration in the hollow body is zero.

2. The OCT probe of claim 1, wherein the support member supports a point that is 3/20 of a total length of the body.

3. The OCT probe of claim 1, wherein a lens is additionally provided in the inner space, the lens being positioned in front of one end of the optical fiber so as to collect the light emitted from the optical fiber.

4. The OCT probe of claim 1, wherein the base has cable slits in an outer surface thereof, the cable slits being cut open a predetermined depth in a longitudinal direction such that the cables connected to the electrodes are inserted into and seated in the cable slits.

* * * * *